United States Patent [19]
Zuest

[11] Patent Number: 5,254,005
[45] Date of Patent: Oct. 19, 1993

[54] DENTAL IMPLANT SYSTEM AND METHOD

[76] Inventor: Max Zuest, 595 San Fernando, San Diego, Calif. 92106

[21] Appl. No.: 751,661

[22] Filed: Aug. 22, 1991

Related U.S. Application Data

[63] Continuation of Ser. No. 436,432, Nov. 14, 1989, abandoned.

[51] Int. Cl.⁵ .................................................. A61C 8/00
[52] U.S. Cl. .................................... 433/173; 433/174
[58] Field of Search ............. 433/172, 173, 174, 141, 433/144, 201.1, 167

[56] References Cited

U.S. PATENT DOCUMENTS

| | | | |
|---|---|---|---|
| 3,514,858 | 4/1969 | Silverman | 433/174 |
| 3,905,109 | 9/1975 | Cohen et al. | 433/174 |
| 4,177,562 | 12/1979 | Miller et al. | 433/174 |
| 4,738,622 | 4/1988 | Kawahara et al. | 433/169 |
| 4,744,755 | 5/1988 | Ross | 433/173 |
| 4,856,994 | 8/1989 | Lazzara et al. | 433/173 |
| 4,906,191 | 3/1990 | Söderberg | 433/213 |
| 4,907,969 | 3/1990 | Ward | 433/173 |
| 5,022,860 | 6/1991 | Lazzara et al. | 433/174 |

*Primary Examiner*—Cary E. O'Connor
*Assistant Examiner*—Cindy A. Cherichetti
*Attorney, Agent, or Firm*—Brown, Martin, Haller & McClain

[57] ABSTRACT

An implant assembly and method is provided, as well as a system and method for exposing an embedded implant after osseointegration has taken place. The implant assembly comprises an implant member for embedding in the jaw and a rest factor member for securing to the implant member, the rest factor member having an upper rest surface just above the tissue level for opposing an overlying portion of a prosthesis anchored elsewhere in the jaw to form a nonretentive rest or support for accepting down pressure from the prosthesis. The implant member is relatively short and can be installed in distal jaw regions without interference with the mandibular nerve, and has an undersurface having a shape designed for stable integration with the bone while resisting sidesway. The method includes cutting out a bore in the jaw for receiving the implant, inserting the implant and an attached healing screw in the implant, closing the implant site and allowing osseointegration to take place over an extended period, and subsequently uncovering the implant site, removing the healing screw, and securing the rest factor member in the implant.

15 Claims, 4 Drawing Sheets

DENTAL IMPLANT SYSTEM AND METHOD

This is a continuation of application Ser. No. 07/436,432, filed Nov. 14, 1989, now abandoned.

BACKGROUND OF THE INVENTION

The present invention relates to a dental implant system and method.

Dental implants are embedded in the jaw bone and serve to anchor one or more artificial teeth or dentures. Most implant systems involve a relatively long implant cylinder which is placed into a custom bored hole in the jawbone, then left for several months to allow healing and bone integration. Then the implant must be exposed for attachment of a dental prosthetic appliance such as a crown, denture, partial denture or bridge. This generally involves the dentist cutting out a flap of tissue which is peeled back to expose the implant, and secured by sutures after installing the prosthesis. This results in a relatively large area of trauma with a certain degree of pain to the patient and risk of post-operative infection.

Another problem with conventional implants is their length, which makes them difficult to implant in the distal jaw region, where there is insufficient depth to enable their insertion without interference with the mandibular nerve, without the assistance of a dental surgeon to locate the precise position of the nerve and ensure that the implant does not interfere with it. A shorter cylindrical implant would not normally be suitable since it would provide insufficient "hold" and would likely become loosened with time if anchored to a denture or bridge. Also, side to side forces on the implant lead to bone erosion and trauma. Thus, dentures or bridges are often not anchored at the rear of the jaw. However, this has the disadvantage that trauma to the tissue and underlying bone beneath the denture occurs as a result of the denture repeatedly impacting the bone, particularly with long dentures which will tend to tilt or rotate about their attachment or anchor points during chewing or other jaw motions. This biting pressure can result in bone erosion or resorption down to the level of the nerve.

SUMMARY OF THE INVENTION

It is an object of this invention to provide an improved dental implant system and method which is less likely to cause significant tissue trauma and which reduces bone erosion as a result of denture wear.

It is a further object of this invention to provide an improved system and method for exposing an implant site after osseointegration has taken place.

According to a first aspect of the present invention, a dental implant assembly is provided which comprises a first, implant member for implanting in the jaw bone in the region behind the first bicuspid in the area of the mandibular nerve canal, and a second member or rest factor for attachment to the implant member. The two members have cooperating releasable securing devices for releasably securing them together, preferably comprising a screw threaded bore the implant member and a corresponding threaded portion on the rest factor member. The rest factor member projects up to just above the level of the tissue overlying the jaw bone and has an upper surface opposing an overlying portion of a prosthesis anchored elsewhere in the jaw to form a rest for the prosthesis which accepts down pressure only, and which acts as a support to prevent or restrict bone erosion. The implant member is relatively short and has a selected height less than the depth of the mandibular nerve at the implant site, so that it can be embedded in the bone without risk of interference with the nerve. At the same time, the implant member is as wide as possible, and preferably has the maximum diameter possible according to the width of the patient's alveolar ridge at the implant site. The implant member diameter is preferably selected to be 1 mm less than the available alveolar ridge or bone width at the implant site. Implant members in a range of different heights and diameters are preferably provided to meet the requirements of a range of patients. Preferably, implant members with heights in the range from 2 to 4.5 mm are provided, to allow for patients whose jawbone is already eroded to some extent. Implant members with diameters ranging from about 4 mm to 6 mm may be provided.

Since the implant member is of relatively large diameter, it has a relatively large surface area resisting downward forces. In the preferred embodiment of the invention, the implant member is a thin, disc-shaped member with a downwardly depending annular rim which engages in a corresponding annular recess drilled out in the bone to resist sideways movement of the implant. The implant member also has a central, downwardly depending boss of height equal to or slightly greater than the annular rim. This will also resist sideways movement of the implant during osseointegration, and also provides additional depth for securing the rest factor to the implant member. A bore of corresponding shape to the undersurface of the implant member is drilled out in the jawbone at the implant site, so that when the implant member is positioned in the bore, the peripheral rim will provide stabilization of the member against lateral movement during the osseointegration period. The shape of the undersurface of the implant provides a large area of bone to implant contact for osseointegration, and significant resistance to both lateral and downward forces both during and after the osseointegration period.

Since the rest factor is not anchored to the prosthesis, the risk of jaw bone erosion or damage as a result of upward forces is reduced. However, the rest factor does accept down pressure as a result of biting pressure of the denture, and will thus reduce the risk of trauma to the tissue and jawbone erosion as a result of pressure. The localized contact between the rest factor and the underlying bone via the implant member reduces or substantially eliminates pressure trauma on the entire bone.

If desired, the upper surface of the rest factor and the opposing portion of the prosthesis may be provided with opposing, non-retentive mating formations, such as opposing slightly convex and concave formations, for guiding the prosthesis against the rest factor. However, these formations do not provide any upwards retention of the prosthesis. A series of such rest factors may be provided at appropriate locations in the jaw where maximum down pressure from a denture is encountered, considerably reducing the discomfort of denture use and reducing the risk of tissue and jawbone damage as would result from conventionally anchored dentures.

According to another aspect of this invention, a method of installing a rest factor in the jaw to accept down pressure from a denture anchored elsewhere in the jaw is provided, which comprises the steps of:

cutting out a bore in the jawbone at a selected location in the region behind the first bicuspid, the bone being shaped to receive an implant member;

installing the implant member in the prepared bore with a healing screw mounted in the implant member;

closing the implant site and leaving the implant to integrate with the bone over an extended time period;

uncovering the implant site;

removing the healing screw; and securing a rest factor member in the implant member, the rest factor having an upwardly projecting boss projecting to just above the tissue level.

The rest factor may be preformed with a suitable rest surface in incremental heights, in which case the procedure after removing the healing screw comprises selecting an appropriate height rest factor and securing the selected rest factor in the implant member.

Since the annular member is relatively short with a relatively large diameter, it can be anchored securely in the jawbone without needing a deep bore to be drilled out. The implant will be shorter and wider than conventional cylindrical implants, and thus can be used at the back or posterior mandible of the jaw where the nerve position prevents or restricts the use of long implants. This implant is particularly suitable for positioning a rest factor in the second molar area in conjunction with implant dentistry where cantilevered bridges or anterior implants need support or in other places where a rest factor is needed in dentistry. The implant requires less bone to be drilled out than conventional cylindrical implants, reducing or minimizing bone loss, and is able to accept hundreds of pounds of down pressure from an overlying denture or prosthesis.

According to another aspect of this invention, a method of recovering an implant after bone integration is provided, which comprises piercing the tissue overlying a healing screw secured to the implant with a pointed end of a locating guide tool, probing the implant site with the pointed end until it engages a hole in the top of the healing screw, inserting the pointed end into the hole, utilizing a tissue punch centered on the guide tool to cut out a plug of tissue directly over the implant, and subsequently removing the healing screw.

Thus, the locating tool and tissue punch can be removed together from the implant site, carrying with them the tissue plug to expose the healing screw for removal with a separate tool. The implant is then exposed for secondary healing or restoration procedures while a minimum amount of tissue has been disturbed and little or no suturing is required. This considerably reduces the trauma, secondary tissue healing, discomfort to the patient, and risk of infection.

According to another aspect of the present invention, an implant locating and exposing tool is provided, which comprises an elongate shaft having a head at one end and a locating probe at the opposite end having a sharp end for probing the tissue over an implant site to locate a central hole in the top of a healing screw, and a cutter member mounted on the elongate member with its cutting face facing in the same direction as the locating probe, the cutter member being movable along the elongate shaft to cut out a plug of tissue overlying a healing screw.

Thus, the healing screw can be located and the overlying tissue removed in one step, without having to cut out a relatively large flap of tissue.

The healing screw may be provided with a concave upper surface so that the locating probe will be guided towards the central opening.

The implant system and method described above provides a rest surface for an overlying cantilevered bridge or denture which is anchored elsewhere in the jaw, on which the denture can rest and which accepts down pressure from the denture, reducing tissue trauma. Rest surfaces may be provided wherever needed, in conjunction with the conventional implants and anchors used for securing the denture or prosthesis in the jaw. The improved implant recovery tool and method produces minimal trauma when exposing a previously embedded implant for subsequent connection to either a rest factor or to a conventional anchor.

BRIEF DESCRIPTION OF THE DRAWINGS

The present invention will be better understood from the following detailed description of some preferred embodiments of the invention, taken in conjunction with the accompanying drawings, in which like reference numerals refer to like parts, and in which.

DESCRIPTION OF THE PREFERRED EMBODIMENT

Figures 1, 2, 3, 4A, 4B, 5:
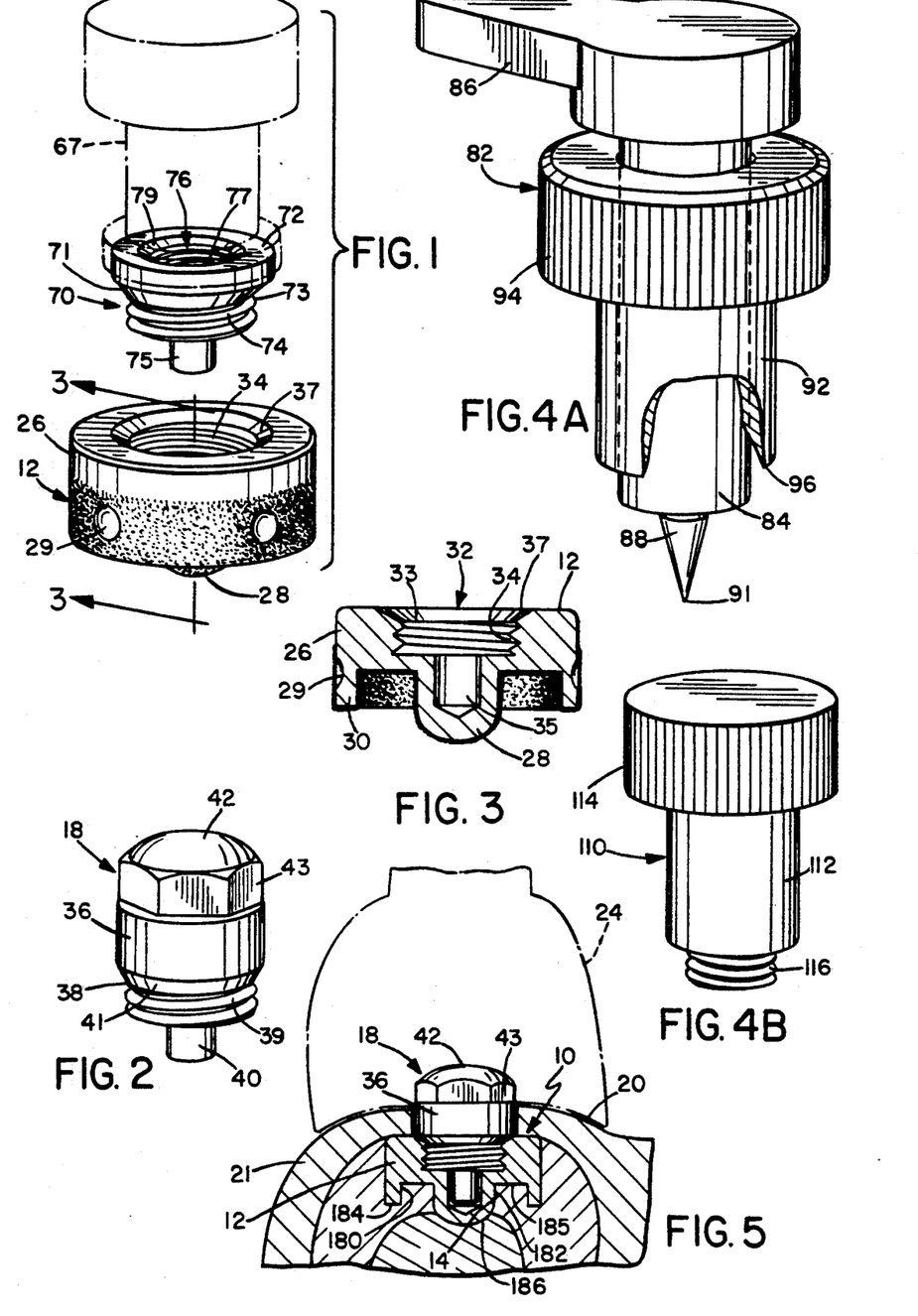
FIG. 1 is a perspective view of the separated implant and healing screw components of an implant assembly according to a first embodiment of the invention.
FIG. 2 is a perspective view of a rest factor of the implant assembly.
FIG. 3 is a sectional view of the implant taken on line 3—3 of FIG. 1.
FIG. 4A is a perspective view of a preferred embodiment of the implant locating tool according to another aspect of the invention.
FIG. 4B is a perspective view of a healing screw removal tool.
FIG. 5 is a sectional view through a typical jawbone with a finished implant in place and a rest factor inserted.
Figure 6:
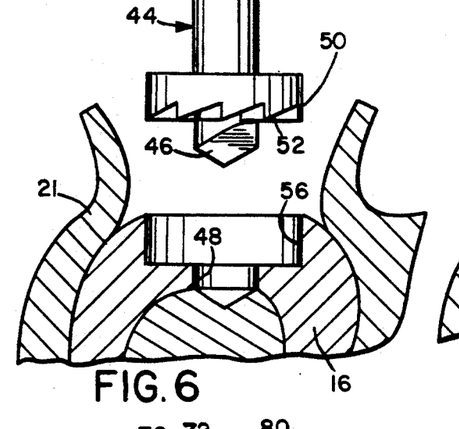
FIG. 6 is a jawbone section illustrating the initial drilling set up for an implant.

FIGS. 1 to 3 and 5 of the drawings illustrate an implant assembly 10 according to a first embodiment of the present invention, as well as a method of installing the assembly in the jaw. As best illustrated in FIG. 5, the implant assembly 10 basically comprises an implant 12 for insertion into a suitably prepared bore 14 in the jawbone 16, where it is secured in place by osseointegration as is known in the field of implant dentistry, and an extension member or rest factor 18 secured to the implant 12 and extending up to slightly above the level 20 of the tissue or gum 21 to form a rest surface 42 for an overlying denture or bridge 24 which is anchored elsewhere in the jaw.

As best illustrated in FIGS. 1 and 3, implant 12 comprises a thin, annular member or disc 26 having a central spigot or downward extension 28 projecting from one of its faces and an annular peripheral rim 30 projecting from the same face. A central bore 32 extends from the opposite face into the spigot 28, as illustrated in FIG. 4. The bore 32 has a larger diameter upper portion 33 having internal screw threads 34 extending along its length with a taper 37 at its upper end for added strength to hold the threaded engagement. The lower end of bore 32 comprises a smaller diameter lower portion 35 extending into spigot 28 for centering parts mating with implant 12 and preventing cross-threading of the threaded engagement. The implant will be of metal or any suitably rigid material as is normally used for dental implants, for example surgical titanium alloy. The implant preferably has spaced indents 29 on its outer surface for resisting rotation.

Figure 11:
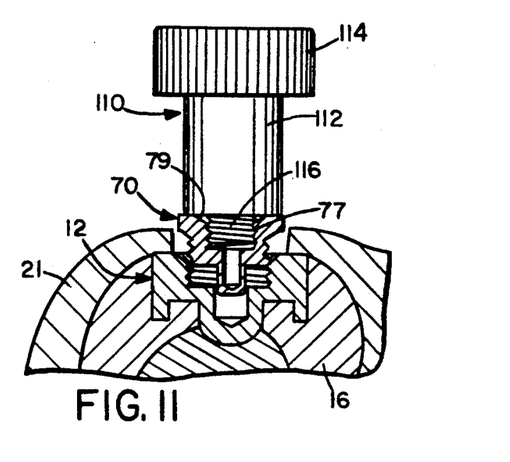
FIG. 11 illustrates the removal of the healing screw.

Also illustrated in FIG. 1 is a healing screw 70 for insertion in the implant member during the osseointegration process. Healing screw 70 has a relatively short head portion 72 and downwardly depending shaft portion 73 for engagement in the bore 32 of implant 12. Portion 73 has a screw threaded larger diameter upper part 74 for threaded engagement in bore portion 33, the upper part 74 having a taper 71 at its upper end matching the taper 37 at the upper end of the implant bore 32 for support and seating of the screw 70 in bore 32. The lower end of portion 73 comprises a smaller diameter, cylindrical lower part 75 for fitting into lower portion 35. The upper end face of the head portion has a central, tool receiving bore 76 for receiving the end of a suitable tool for inserting the arrangement in the bore in the jawbone, and for subsequently receiving the end of a locating or removing tool as will be explained in more detail below. If desired, the upper end face of screw 70 may have a concave or dish-shaped depression 79 surrounding bore 76. The bore corresponding to bore 76 in FIG. 1 is illustrated in FIG. 11 receiving a screw threaded upper portion 77 and has a downward depending cylindrical centering extension corresponding to extension 75 in FIG. 1. The threads in upper portion 77 are of opposite hand to those of screw threaded portion 74. In the embodiment illustrated in the drawings, portion 74 has a right hand thread while portion 77 has a left hand thread. The healing screw may be provided in a range of sizes, but in each case the height of the head portion is of the order of 1 mm or less.

The extension or rest factor member 18 as it appears prior to installation in the jaw is illustrated in FIG. 2. The member comprises a generally cylindrical boss 36 having a projecting shaft 38 at one end dimensioned for mating engagement in the bore 32 of implant 12. Shaft 38 has an upper, larger diameter portion 39 having external screw threads for threaded engagement with the internal screw threads 34 in the upper part 33 of bore 32, and a lower, smaller diameter cylindrical extension 40 for fitting into the lower part 35 of bore 32, as illustrated in FIG. 11. The upper end of shaft 38 has a taper 41 matching the taper 37 at the upper end of the implant bore 32. Member 18 has a curved, slightly convex rest or support surface 42 at its upper end, and an external hex formation 43 for securing it to a suitable tool for insertion into the implant. The member 18 will also be of a suitable dental material such as titanium alloy. Preferably, surface 42 has a relatively small curvature of 10 degrees or less.

Member 18 may alternatively be formed with a concave support surface (not illustrated), or with any suitably shaped upper rest or support surface. Member 18 will be made in a range of heights to allow the dentist to select the appropriate size rest factor for a particular patient's tissue level. The rest factor is selected to project to a distance of no more than ½ to 1 mm above the tissue level when installed in the jaw, and is preferably kept as low as possible so that it acts to accept biting pressures but will not interfere with normal jaw motions.

Figure 12:
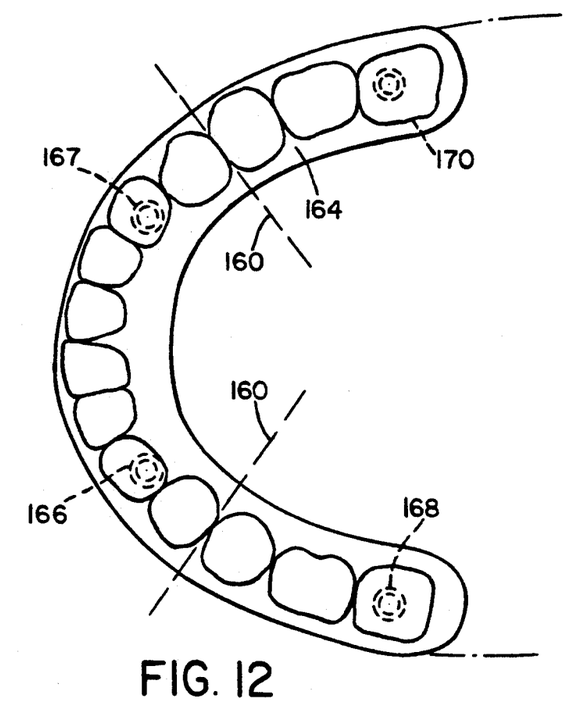
FIG. 12 illustrates the lower half of a patient's jaw with a full denture anchored in place and seated on rest factors in posterior areas on both sides.
Figure 13:
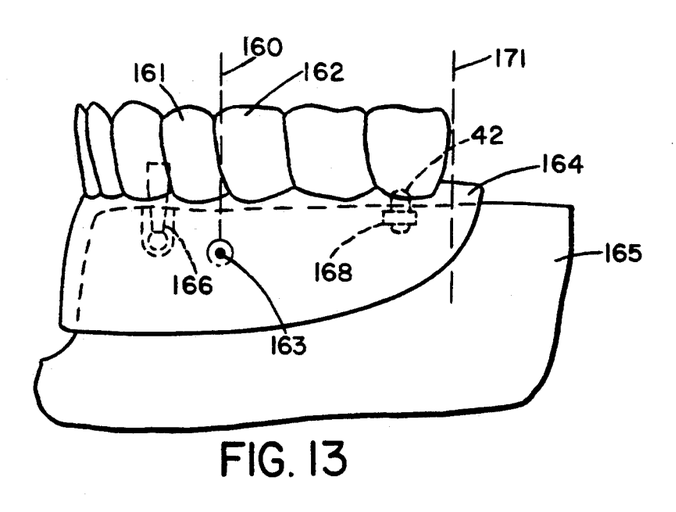
FIG. 13 is a side view of the denture arrangement of FIG. 12.

The implant assembly with the rest surface 42 is used to form a rest or support surface in implant dentistry for a prosthesis anchored elsewhere in the jaw, for example, as illustrated in FIGS. 12 and 13. The implant assembly is designed to be very short or thin so that it can be installed in distal jaw regions to the rear of line 160 in FIGS. 12 and 13, which extends between the first and second bicuspids 161 and 162 and corresponds to the approximate location where the mandibular nerve 163 exits the jawbone. The mandibular nerve extends through the jawbone to the rear of the first bicuspid, making the installation of long implants in this region difficult or impossible without the assistance of a dental surgeon. This problem becomes even more pronounced in patients whose jawbone has already eroded to some extent due to denture wear. Thus, unsecured dentures are common, resulting in bone erosion from biting impacts. This rest factor assembly avoids or reduces such problems. The implant has a relatively large diameter as compared to its height, providing good implant to bone contact and integration, while having only a short penetration into the jawbone. In the preferred embodiment illustrated, the penetration into jawbone is only between 2 to 4.5 mm, depending on the patient's available bone depth, and there is thus little or no risk of interference with the mandibular nerve.

FIGS. 12 and 13 illustrate the assembly implanted in the jaw for cooperation with an overlying denture anchored elsewhere. In FIGS. 12 and 13, a full denture or prosthesis 164 is illustrated, secured to a patient's lower jaw 165 via a pair of anchors 166, 167 mounted in the anterior regions of the patient's jaw, and seated on implanted rest factors 168,170 in the posterior or distal jaw region below the former second molar at each end of the denture. In practice, the rest factor assembly may be installed anywhere between the region corresponding to the former second molar (line 171) and the first bicuspid (line 160). The area to the rear of the line 171 has too many muscles for insertion of an implant. As illustrated in FIG. 13, the rest factors may be provided or preformed with a slightly convex or curved head 42 which projects slightly (around ½ to 1 mm) above the tissue level, although support surfaces of a different shape may be provided. The prosthesis or denture is preferably provided with a corresponding concave surface or depression for seating on the opposing rest factors or surfaces 168 and 170.

Most typical denture anchors allow a limited degree of pivoting or side-to-side motions of the denture with jaw motions so as to reduce stress in the jaw bone areas to which the denture is positively anchored. With relatively long partial or full dentures which extend into the posterior jaw regions, tilting or rotation of the denture about the anchor points with jaw or biting motions will apply pressure or biting force to the underlying tissue and jawbone, causing discomfort and trauma to the underlying bone and tissue, and ultimately resulting in significant bone erosion. The rest surface or surfaces avoid or reduce this problem by accepting down or biting pressure from the denture. Since the rest surfaces are not positively anchored to the denture, they will not be pulled up or from side to side as a result of jaw motions, and will therefore be less likely to cause bone erosion or damage. Additionally, the implant assembly undersurface has a relatively large surface area to resist downward forces and is shaped to resist side movement. The implant assembly is therefore intended to be used at appropriate locations in the jaw which would otherwise be subject to considerable down pressure and potential trauma from an implant such as a full or partial denture or cantilevered bridge. The rest factor surface will be shaped to ensure that it can accept down pressure from an overlying denture in various possible orientations, whatever the angle of the patient's jaw. The support surface prevents excessive force on the tissue, and thus protects the gum tissue from impacting forces which could cause soreness and trauma. Additionally, the rest or support surface prevents or reduces bone erosion by providing support to the distal end of the denture and resisting biting forces.

The implant assembly is designed for implantation at any position in the jaw where a rest factor or surface for a full or partial denture or bridge is needed. Normally, this will be in the posterior jaw, for example in between the first bicuspid and the second molar area, as illustrated in FIGS. 12 and 13, but a rest surface may also be advantageous in other areas. The dimensions of the assembly 10 are selected according to the dimensions of the jaw in the area where the implant is to be used. A range of implant assemblies of different dimensions may be provided for fitting patients having different jaw dimensions. The implant member is designed to provide sufficient anchoring area with the jawbone when embedded in the jaw, while not extending too deeply into the jaw where it might otherwise interfere with the nerve. Thus, it is short and relatively wide. The implant member has a relatively large diameter, larger than typical straight cylindrical implants, but is shorter in length than such implants, preferably having an overall length in the range from 2 mm to 4.5 mm. In one specific example, several different size implants were provided with annular members of 4.25 mm, 5 mm, and 6 mm outer diameter, respectively. The rest factor may have a diameter of 4 mm. The extension or spigot 28 may also be provided in different sizes according to the position in the jaw where it is to be embedded. Central spigots of length between 1 mm and 3 mm may be provided. Also, the central spigot may be omitted in some cases where very little depth is available in the jawbone for embedding the implant. In this case, the rest factor 18 will also have no projection 40. Rest factors having heads in a range of different sizes are also provided, for example, 3 mm, 4 mm and 5 mm. Generally, the overall implant assembly is very short, extending only from 2 to 4.5 mm into the jawbone, while the implant is shaped to have a relatively large bone to implant contact area, as best illustrated in FIG. 5.

As can be seen in FIG. 5, after osseointegration has taken place, there will be a relatively large area of bone to implant integration even though the penetration into the jaw bone is very short. The shape of the underside of the implant will act to provide stability during the osseointegration process, and a strong bone to implant bond resisting lateral and downward forces throughout the lifetime of the implant. The peripheral rim 30 acts to resist sideways movements due to its inner and outer circumferential surfaces 180, while the lower surfaces 184,185,186 of the outer rim 30, upper face, and boss 28 resist vertical, downward forces. The surfaces combine to provide maximum rest factor to bone contact with a relatively short distance of penetration into the jawbone. The indents 29 in the outer surface will resist rotational movements of the implant. Thus, the implant surfaces resist lateral and vertical movements during osseointegration, and the implant effectively becomes fully integrated with the bone.

This implant is sufficiently short to be safely inserted even where some bone erosion has already taken place, with the appropriate height implant member and rest factor being selected according to the bone depth and tissue height of the particular patient.

The method of inserting the implant 12 in the jaw will now be described with reference to FIGS. 6 to 11 of the drawings. This can easily be done by a dentist or dental surgeon. First, a bore shaped to correspond to the shape of member 12 must be cut out. This is done using a series of special cutting burrs. A first water cooled burr or cutter (not illustrated in the drawings) is used to drill a cylindrical guide hole or pilot dimple at the center of a selected site, for example under the second molar area or at the distal end of a cantilevered bridge. The width of the alveolar crest with equal distance on both sides of the pilot dimple is then measured. The largest diameter rest factor implant which will fit within the available width while allowing at least ½ mm of bone on each side of the implant is selected. An internally irrigated implant body drill 44 of diameter matching that of the selected rest factor implant is then selected. Burr 44, illustrated in FIG. 6, has a smaller diameter pilot drill 46 for cutting out a cylindrical bore 48 and a larger diameter portion 50 having an end cutter 52 for drilling out the larger diameter upper end 56 of the bore. The cylindrical portion 50 may be provided with suitable markings or a scale (not shown) so that the dentist can control the depth the drilled bore. However, in the preferred version, the height of portion 50 matches the height of implant member 12. The length of the pilot drill 46 will correspond to the length of spigot 28 of the implant, so that spigot 28 will fit in bore portion 48. The dentist determines the optimum angle and drills in to the bone to a point where the larger diameter portion 50 ends.

Figure 7:
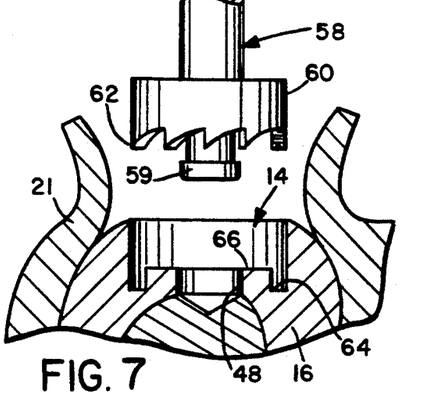
FIG. 7 is a similar view illustrating the final counterboring operation for an implant.

FIG. 7 illustrates the operation of a water cooled guided core drill or burr 58 having a central guide or pilot tip 59 for fitting in the previously drilled bore portion 48 to center the tool on the bore. The tool has a cylindrical central body portion 60 having a downwardly facing annular ring of cutting teeth 62 for drilling out an annular groove or channel 64 around the periphery of the flat or shoulder 66 separating counter bore 56 from the smaller diameter bore portion 48. The length of the teeth controls the depth of groove 64, and will be equivalent to the height of the downwardly depending rim 30 of the implant to be received in the bore. Once the lower face of body portion 60 hits the flat 66, drilling is stopped.

All three cutting tools may be provided with a cage for collecting bone as it is drilled out of the bore. The collected bone may be used for filling any edges or spaces left after insertion of the implant.

After the bore for receiving the implant 12 has been prepared as described above, and debris has been cleaned out in the standard manner, for example by irrigating the site with sterile water or sterile saline, the implant 12 can be inserted. The healing screw 70 is initially secured to the implant.

Figure 8:
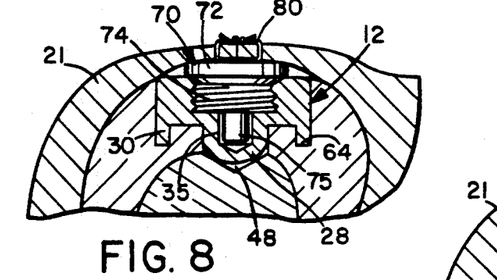
FIG. 8 is a similar view with an implant and healing screw in place and enclosed under tissue for the osseointegration period.

Prior to insertion in the previously prepared bore, the internal faces of the implant will be coated with a suitable bonding agent, such as hydroxyl apatite. These faces may be roughened as illustrated in FIGS. 1 and 3 to increase the bonding area and strengthen the adhesion in the bore 14. A suitable plastic insertion tool 67 (See FIG. 1) having a handle and a gripping end for snap engagement over the head of the healing screw is then used to insert the implant and attached healing screw in the bore. The bore is drilled out to a depth such that the upper end of the implant 12 will be at the bone level when fully inserted, as indicated in FIG. 8, or slightly below that level if desired. For convenience, the insertion tool is preferably a disposable, snap-off plastic member which is supplied in a sealed, sterile package together with the healing screw and implant, the three parts being supplied secured together in the package for easy handling. The insertion tool can be snapped off after the parts have been positioned in the bore.

The tissue or gum 21 is then secured over the implant and healing screw with conventional flap sutures 80. Since the head portion of the healing screw projecting above the implant member is relatively short, little or no bulge will be apparent when the tissue is sewn up. The site is left to heal for several months to allow the implant to osseointegrate, or bond with the surrounding bone. The shape of the implant member is designed for maximum stability in resisting movement during the osseointegration period, due to its relatively large diameter and the peripheral rim 30 as well as spigot 28. These also combine to provide a relatively large bone to implant bonding area after osseointegration. After the integration period, a special locating tool 82, best illustrated in FIGS. 4A, 9 and 10, is used to locate the implant.

The retrieval tool 82 comprises a central shaft 84 with a head or gripping handle 86 at one end. Handle 86 projects to one side of the shaft as indicated. A projecting probe 88 at the opposite end is designed for engagement in the bore 76 of healing screw. The probe has a sharp pointed end 91. A cutter sleeve or tissue punch 92 is slidably mounted on shaft 84. Cutter sleeve 92 has a projecting annular handle or gripping portion 94 and a lower cutting edge 96.

The use of the retrieval tool 82 to locate the implant site will now be explained, with reference to FIGS. 1 and 9. The approximate area of the implant is first located, utilizing radiographic charts and finger palpations. The pointed end 91 of the probe is then used to pierce the tissue 21 at the approximate site of the implant, and is then used as a probe to locate the upper face of the healing screw. Once the screw has been found, the concave recess (if provided) will act as a guide to direct the pointed end to the retrieval hole or bore 76 at the center of the healing screw, as illustrated in FIG. 9, centering the tool on the implant site.

Figure 9:
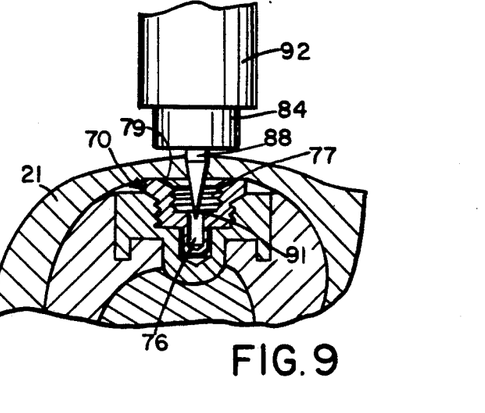
FIG. 9 illustrates the locating of the integrated implant under the issue.
Figure 10:
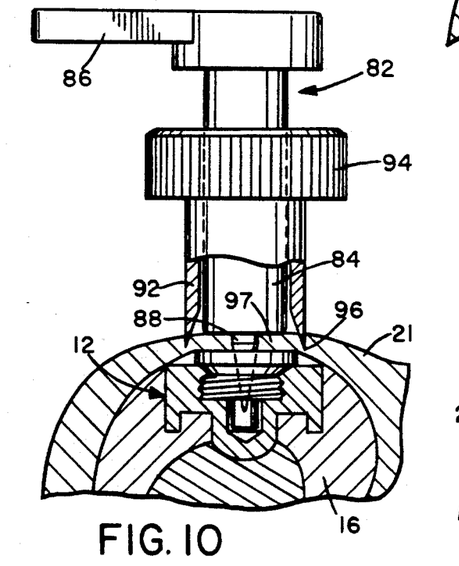
FIG. 10 illustrates the cutting out of a tissue plug overlying the healing screw.

Once the probe has entered bore 76, as illustrated in FIG. 9, the handle 86 of the locating tool is held firmly in one hand to support the tool upright and the tissue punch is turned in a circular motion while pushing it down along the locating tool with a firm pressure. The tissue punch is designed to cut out a plug 97 of tissue directly over the implant. The punch will be stopped when it engages the outer diameter of the healing screw. The locating retrieval tool 82 is then removed together with the tissue punch, simultaneously pulling out the plug of tissue. If the tissue plug does not pull out, it may be removed with forceps.

A separate healing screw removal tool 110 is then used to remove the exposed healing screw. Tool 110 is illustrated in FIG. 4B and 11, and comprises a shaft portion 112 with a head or gripping portion 114 at one end and a threaded portion 116 at the opposite end for threaded engagement in the threaded, upper end portion 77 of bore 76 of the healing screw. The threaded end 116 is threaded counter-clockwise into the healing screw, tightening the tool inside the healing screw and at the same time unscrewing the healing screw from the implant as illustrated in FIG. 11. The implant is thus exposed for secondary healing or restoration procedures.

This technique for exposing or recovery of an embedded implant after healing and osseointegration has taken place removes only a small plug of tissue from immediately above the implant site, avoiding the need to cut out an enlarged flap of the tissue both to locate the implant and to expose the healing screw for removal. Little or no suturing will be required. Thus, considerably less trauma to the tissue is involved, reducing the healing time and the risk of infection. Also, the healing screw is located and the tissue plug may be removed simultaneously with one tool, simplifying the procedure and reducing the time involved. The method involves the use of a specialized healing screw with a bore in its upper surface, together with a special locating and retrieval tool. It may be used not only for location of the implant 12 as described above, but also for locating any conventional cylindrical implants in implant dentistry, replacing the conventional healing screws of such implants with a healing screw as illustrated in FIG. 1 but having a stem or shaft designed for fitting into the implant bore. Although in the preferred embodiment described above, the upper end of the retrieval bore 76 in the upper face of the healing screw is screw threaded, it may alternatively be hexagonal with the retrieval tool having a corresponding hexagonal portion for mating engagement in the bore.

As an additional aid in locating the embedded implant, a thread or wire may be left projecting from the heading screw through the suture area, so that the location may be found easily after healing. Alternatively, the tissue overlying the implant may be marked with a suitable dye. However, it is expected that such markers will not normally be required, the dentist locating the general implant site by feel before piercing the tissue with the probe.

The same implant recovery tools may be used for any selected implant size, since the dimensions of bore 76 in the healing screw will be identical.

Once the healing screw has been removed and the exposed surface of the implant suitably cleaned and prepared, the appropriate rest factor 18 is inserted into the implant. The rest factor 18, in addition to providing a rest surface, also acts as a secondary tissue healing insert. The rest factor is selected with a head height so that it will project just above the patient's tissue level when installed. The shaft 38 of rest factor 18 is screwed into bore 32 of implant 12, as indicated in FIG. 5, with the mating surfaces first being coated with a suitable bonding agent.

Although the rest factor in the preferred embodiment has a head portion preformed in a range of heights, it may alternatively be provided with a longer extension piece which projects above the tissue level 20 when the member 18 is fully inserted. In this case, the dentist marks around the periphery of the selected member 18 at the tissue height, and removes the member from the implant. A suitable temporary cover or crown of a standard nature may be fitted into implant 12 at this point.

The dentist then mounts the member 18 in a previously prepared cast of the patient's jaw, and machines or cuts away the upper face of member 18 to provide the desired rest surface 22 at the tissue level 20, as determined by the markings made while the member was mounted in the patient's jaw. The cut away surface may be slanted or inclined according to the angle of the patient's tissue or gum. This allows the height to be customized for minimal side torque. The shape of the rest surface 22 may be of the dentists choice. For example, it may be concave, while the denture or prosthesis with which it is to cooperate has a corresponding convex area or bump 95 for fitting into the concave depression on the rest surface, so that the rest factor or member 18 accepts down pressure from the denture without any retention. However, in the preferred embodiment, members 18 with ready-made ball-shaped or other shape heads of various sizes in a range of tissue heights are provided to avoid the need for machining on site by the dentist.

This procedure may be utilized to implant one or more rest factors at any suitable location in the jaw, depending on the denture pressure points, for example as illustrated in FIGS. 12 and 13.

Figure 14:
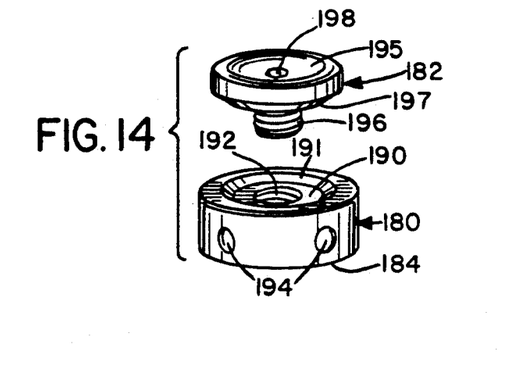
FIG. 14 is a perspective view of the separated implant and healing screw components of an implant assembly according to a second embodiment of the invention.

FIG. 14 of the drawings illustrates an alternative embodiment of the implant assembly which is much thinner than that of FIGS. 1 to 3 and 5 and which will therefore project only a minimal distance into the jawbone, further reducing the risk of interference with the nerve. This implant assembly is useful for providing a rest surface at a desired location in any patient's jaw, whether or not previous bone erosion is a factor, but is particularly useful in patients having significant bone erosion where very little depth is available for implants.

Figure 15:
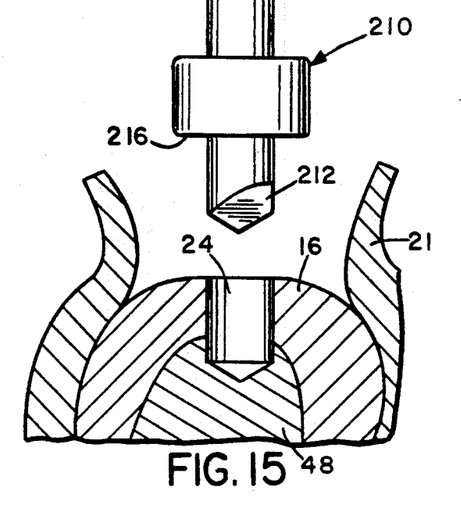
FIG. 15 is a jawbone section illustrating the initial drilling set up for the implant of FIG. 14.
Figure 16:
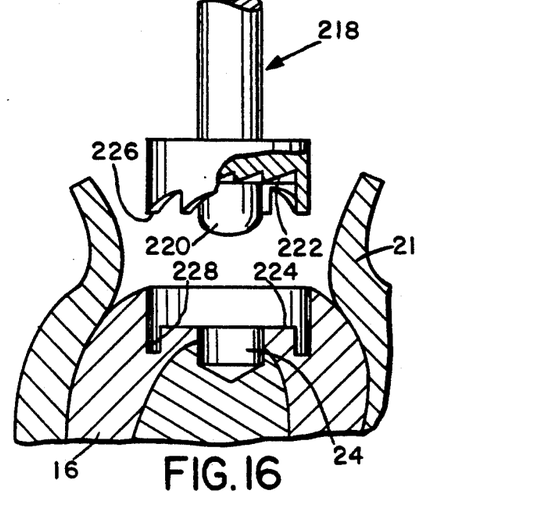
FIG. 16 is a similar view to FIG. 15 illustrating the next step in the drilling procedure.
Figure 17:
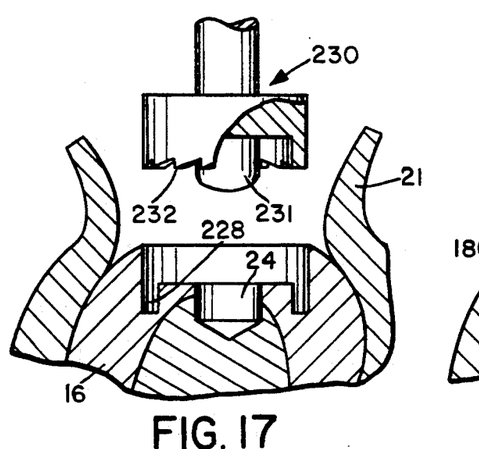
FIG. 17 is a similar view illustrating the finishing step in the boring operation.
Figure 18:
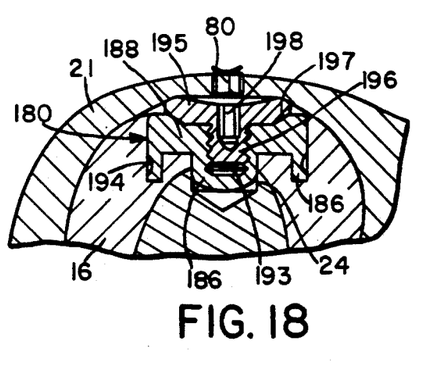
FIG. 18 is a similar view illustrating the implant and healing screw in place and enclosed under tissue for the osseointegration period.

FIG. 14 illustrates an implant member 180 and healing screw 182 of an implant assembly according to a second, modified embodiment of the invention. FIG. 18 illustrates the implant member 180 and healing screw 182 of FIG. 14 implanted in the jawbone during the osseointegration process, while FIGS. 15 to 17 illustrate a modified method of forming a bore in the jawbone for receiving the implant.

As illustrated in FIGS. 14 and 18, implant member 180 is a flat disc-like member having an undersurface of similar shape to the undersurface of member 12 in the first embodiment. However, the peripheral rim 184 and central spigot 186 are approximately the same length in this embodiment, so that the spigot 186 does not project downwardly below the lower end of rim 184. Preferably, member 180 has a total height of around 2 mm while its peripheral rim 184 projects around 1 mm below the undersurface of disc part 188. The member 180 is provided in a range of diameters, preferably 4.25 mm, 5 mm and 6 mm, for patients having varying alveolar ridge widths. As in the first embodiment, the maximum diameter possible implant member is selected for the patient dependent on the available space, i.e., the alveolar ridge width. The rim 84 is relatively thin, and in one particular example had a thickness of the order of 0.4 mm.

The member 180 has a recess 190 in its upper surface with a taper 191 extending around the outer periphery of the recess. A central, straight cylindrical bore 192 extends from the center of recessed area 190 into the spigot 186, and bore 192 has screw threads 193 extending along its length. Member 180 is made of the same material as the implant 12 of the first embodiment. As in the first embodiment, circular or rounded indents 194 are provided on the outer surface of member 180 to resist rotational movement after implantation. Between 6 and 8 equally spaced indents may be provided, for example.

Healing screw 182 has a relatively short head portion 195 and a downwardly depending, screw threaded shaft portion 196 for mating engagement in the bore 192 of implant member 180, as illustrated in FIG. 18. The undersurface of head portion 195 seats in recessed area 190 and has a tapered annular surface portion 197 for seating on taper 191 around the recessed area 190, for accurate seating of the screw in bore 192. The upper surface of head 195 has a central, tool receiving bore 198 for receiving the end of a suitable tool for inserting the arrangement in a previously prepared bore in the jawbone, and also for receiving the end of locating tool 82 as described above in connection with the first embodiment of the invention. Bore 198 is of hexagonal cross section, and is designed to be removed by a suitable removal tool having a hexagonal end after location by tool 82.

The rest factor or member of the second embodiment is not illustrated in the drawings but will be similar or equivalent to rest factor 36 as illustrated in FIGS. 2 and 5 of the drawings apart from its lower surface and downwardly depending shaft portion, which will be identical to lower surface and shaft portion of the healing screw 182 for mating engagement in the bore 192 in implant member 180 after osseointegration is complete.

The modified method of inserting insert member 180 in the jaw will now be described with reference to FIGS. 15 to 17 of the drawings. This procedure can easily be carried out by a dentist, although a dental surgeon may also perform the procedure if desired. After the tissue overlying the implant site has been cut, a pilot dimple is formed at the center of the selected site. The width of the alveolar crest or ridge at the implant site is measured, and the largest possible diameter implant which will fit within the available width while leaving at least ½ mm of bone on each side is selected.

A bore matching the selected implant dimensions is then accurately drilled out using a series of three internally irrigated drilling burrs. The first burr 210 has a straight pilot drill 212 for drilling out a cylindrical bore 214 to a desired depth at the implant site, as determined by stop 216, as illustrated in FIG. 15. Preferably, bore 214 will be slightly longer than the implant member, for example 3 mm. A second burr 218 is designed to cut out the desired bore shape to match the shape of the undersurface of implant member 180, as illustrated in FIG. 16. Burr 218 has a central, non-cutting guide or spigot 220 for fitting into previously drilled bore 214 for centering purposes, a first cutting surface 222 for cutting down to the level of flat 224, and an annular, downwardly projecting rim of cutting teeth 226 for cutting out part of annular recess 228 for receiving the annular rim 184 of the implant member. Preferably, teeth 226 are designed to cut recess 228 to a depth of ½ mm. The final burr 230 is illustrated in FIG. 17 and is designed to finish and smooth the surfaces of recess 228. Burr 230 also has a central guide 231 and an annular rim of finer cutting teeth 232 which cut the final ½ mm of the recess to a total depth of around 1 mm, and which smooth and finish the cut surfaces.

The finished bore of FIG. 17 is cut to very precise dimensions by the series of cutting drills so that the implant member can be accurately seated in the bore as illustrated in FIG. 18 after suitable treatment of the surfaces and application of bonding agents. The gap below spigot 186 does not affect the integration process and will soon fill in with bone. The accurate, close fitting of peripheral rim 184 into recess 228 provides great stability and resistance against any sideways movement during the three month or more osseointegration period, so that a good bone to implant bond can be produced in spite of the minimal length of the implant.

After osseointegration is complete, the site is located and the healing screw 182 exposed and removed as described above in connection with the first embodiment of the invention. The rest factor (not illustrated) is inserted into the implant member as described in connection with the previous embodiment.

In both of the embodiments described above, the shape of the undersurface of the implant ensures that there will be little or no side sway either during or after the osseointegration period. This results from the downwardly projecting peripheral rim, having inner and outer circumferential surfaces which combine to resist any sideways forces. This resistance to sidesway is enhanced by the spigot 186 which also acts to resist sideways movement. The relatively large diameter of the implant provides a large area of downwardly facing surfaces which together resist downward forces on the implant assembly, further increasing the stability of the implant and acting to absorb biting pressures. The implant is selected to be of the maximum possible diameter according to the bone width available for implantation in a particular patient. The indents 29,194 will act to resist rotational movements during and after osseointegration. The combined effect of the shape of the undersurface of the implant and its relatively large surface area is to produce a very stable implant with minimal penetration into the bone.

Although the implant member is illustrated as implanted so that its upper surface is at the bone level, it may be implanted to a lesser depth if the patient has a large amount of bone erosion or resorption. For example, if there is only 1 mm bone depth available for implantation without fear of interference with the nerve, the implant is simply installed to 1 mm in depth so that approximately 1 mm. projects above the bone level.

However, it will still have sufficient holding power to remain in position since the undersurface, and particularly the peripheral rim, will position the implant during osseointegration and bond to the surrounding bone to resist sideways and downwards forces. Since it is not anchored to any overlying body, upwards forces do not have to be resisted. Thus, sufficient bonding area is provided to resist any loosening during normal wear.

This implant assembly avoids the problems of implantation in areas to the rear of the second molar since the implantation depth is significantly reduced while still providing sufficient bonding area positioned to provide a stable, fully integrated implant. The rest surface will act to resist the effects of biting pressure from overlying dentures on the jawbone, so that jawbone erosion as the result of such pressure is significantly reduced or eliminated. Additionally, denture comfort will be increased since damage or trauma to the tissue or gum will be reduced.

This implant system and method may be used in any implant procedure where a denture or prosthesis of more than one tooth is involved, and is particularly useful in posterior areas of the jaw where the implant depth is limited, for example the second molar area, and in conjunction with anterior implants or cantilevered bridges. The implant has a relatively short penetration into the bone, so that it can be installed in regions to the rear of the first bicuspid without fear of interference with the nerve, yet has sufficient anchoring surface area to integrate with the bone and accept down pressure of two to three hundred pounds from an overlying denture or prosthesis. Since the implant is not positively anchored to the prosthesis, it does not have to resist large upward or sideways forces, reducing the risk of bone erosion. At the same time, the rest factor will reduce the trauma to underlying tissue and reduce or eliminate bone erosion from the overlying denture by accepting the downward pressure from the denture.

The implant recovery method and tool described above will eliminate the need to locate and expose osseointegrated implants by a surgical flap technique. The locating tool and guided tissue punch accurately locate the implant with minimal trauma, and remove only a plug of tissue directly above the implant sufficient to expose the healing screw for removal. The amount of trauma and bleeding is reduced and the tissue around the implant site remains virtually intact.

Although some preferred embodiments of the present invention have been described above by way of example only, it will be understood by those skilled in the field that modifications may be made to the disclosed embodiments without departing from the scope of the invention, which is defined by the appended claims.

I claim:

1. A combined denture and support assembly, comprising:

a denture of more than one tooth;

an anchor securing one ned of the denture to the jawbone;

support means for freely supporting a distal region of the denture at a selected location to the rear of the first bicuspid, the support means comprising a first, short part for embedding in the jawbone at the selected location and a second part for projecting up to at least the tissue level, the second part having an upper rest surface for non-retentively supporting the denture and for accepting biting pressure from the denture; and said support means has a height no grater than its outer diameter.

2. A method of installing a rest factor in the jaw to accept down pressure from a denture anchored elsewhere in the jaw, comprising the steps of: cutting out a bore in the jaw at a selected location to the rear of the first bicuspid, the bore being shaped to receive a selected implant member and having a lower end spaced above the location of the mandibular nerve; installing the implant member with an attached healing screw into the bore;
   closing the implant site and leaving the implant to integrate with the bone over an extended period;
   uncovering the implant site and removing the healing screw;
   securing a rest factor member to the uncovered implant member, the rest factor member having an upper, continuous rest surface which projects at least up to the tissue level; and
   non-retentively seating a portion of an overlying denture on the rest surface.

3. The method of claim 2, further including the steps of measuring the width of the alveolar ridge at each side of the implant site prior to cutting out the bone, and selecting an implant member of maximum possible diameter to fit in the available space at the implant site from a range of implant members of different diameters.

4. The method of claim 3, wherein the selected implant member diameter is approximately 1 mm less than the alveolar ridge width.

5. The method of claim 2, wherein the step of securing a rest factor member to the uncovered implant member comprises selecting a rest factor member having a head of appropriate height corresponding to between ½ to 1 mm greater than the tissue height at the implant site from a series of rest factor members having heads corresponding to a range of tissue heights, and securing the selected preformed rest factor member to the implant member.

6. An implant recovery assembly, comprising:
   a healing screw having a head portion with a recovery bore in its upper face and a downwardly depending tail portion for mating engagement in a bore in an implant member for embedding in a bore in the jawbone; and
   a recovery tool having a head portion and a downwardly depending probe portion for mating engagement in said recovery bore in the healing screw, the probe portion having a pointed end for piercing tissue overlying the site of a previously embedded implant and healing screw after osseointegration has taken place, the pointed end further comprising probe means for locating the recovery bore in the healing screw.

7. The assembly as claimed in claim 6, wherein the upper face of the healing screw comprises guide means for guiding said pointed end of said probe portion towards said recovery bore.

8. The assembly as claimed in claim 7 wherein said guide means comprises a concave recess in said upper surface centered on said recovery bore.

9. The assembly as claimed in claim 7, wherein said recovery tool further comprises an elongate central shaft between said head portion and probe portion, and a tissue punch sleeve slidably mounted on said shaft, said sleeve having a handle portion and a downwardly facing cutting edge dimensioned for cutting out a plug of tissue overlying said healing screw.

10. The assembly as claimed in claim 9, wherein said head portion includes a handle member projecting transversely to the longitudinal axis of said tool for gripping by an operator with one hand while operating said tissue punch sleeve with the other hand.

11. A method of implanting an implant member in the jaw and subsequently exposing the member after healing for subsequent procedures, the method comprising the steps of:
   cutting out a bore in the jaw shaped and dimensioned to receive at least the lower part of a selected implant member; inserting the implant member with a healing screw releasably attached to the implant member into the bore; closing the tissue over the implant site; allowing the implant member to osseointegrate over an extended period of time;
   piercing the tissue overlying the healing screw with a pointed end of a locating and recovery tool;
   probing the implant site with the pointed end of the tool to locate a bore in the upper surface of the healing screw;
   inserting the pointed end of the tool into the bore in the healing screw;
   moving a tissue punch centered on the recovery tool downwards to cut out a plug of tissue directly over healing screw;
   removing the recovery tool and tissue plug from the implant member to expose the implant member for procedures.

12. A method of locating and exposing an implant member previously embedded in the jaw with a healing screw attached after osseointegration has taken place, comprising the steps of:
   piercing the tissue overlying the implant site with the pointed end of a probe of a locating tool;
   probing the implant site with the pointed end of the probe to locate a recovery bore in the upper surface of the healing screw;
   inserting the probe into the recovery bore;
   moving a tissue punch centered on the locating tool downwardly, to cut out a plug of tissue overlying the healing screw; and
   removing the healing screw from the implant member to expose the implant member.

13. An implant locating tool assembly, comprising:
   an elongate shaft having a head at one end and a locating probe projecting from the opposite end, the probe having a pointed end for piercing tissue over an implant site, and for engagement in a pilot bore in the top of a healing screw attached to an implant; and
   a cutter sleeve slidably mounted on said elongate shaft, said sleeve having a handle portion and cutter means at its lower end facing away from said handle portion for cutting out a plug of tissue overlying an implant site.

14. The assembly as claimed in claim 13, wherein said head includes a handle portion projecting to one side of said shaft.

15. The assembly as claim in claim 13, further including a healing screw removal tool having securing means at one end for mating engagement in a pilot bore in the top of a healing screw attached to an implant.

* * * * *

UNITED STATES PATENT AND TRADEMARK OFFICE
CERTIFICATE OF CORRECTION

PATENT NO. : 5,254,005
DATED : OCTOBER 19, 1993
INVENTOR(S) : MAX ZUEST

It is certified that error appears in the above-indentified patent and that said Letters Patent is hereby corrected as shown below:

```
Column 14, line 58, delete "ned" and insert --end--.

Column 15, line 1, delete "grater" and insert --greater--.
```

Signed and Sealed this

Seventh Day of June, 1994

Attest:

BRUCE LEHMAN

*Attesting Officer*    *Commissioner of Patents and Trademarks*